(12) United States Patent
Makkapati et al.

(10) Patent No.: US 9,968,282 B2
(45) Date of Patent: May 15, 2018

(54) MEDICAL DEVICE OR SYSTEM FOR MEASURING HEMOGLOBIN LEVELS DURING ACCIDENTS USING A CAMERA-PROJECTOR SYSTEM

(71) Applicant: KONINKLIJKE PHILIPS N.V., Eindhoven (NL)

(72) Inventors: Vishnu Vardhan Makkapati, Ongole (IN); Michael Mathias Spaeth, Stuttgart (DE); Shrutin Ulman, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 165 days.

(21) Appl. No.: 14/647,834

(22) PCT Filed: Dec. 2, 2013

(86) PCT No.: PCT/IB2013/060564
§ 371 (c)(1),
(2) Date: May 28, 2015

(87) PCT Pub. No.: WO2014/091358
PCT Pub. Date: Jun. 19, 2014

(65) Prior Publication Data
US 2015/0297119 A1 Oct. 22, 2015

Related U.S. Application Data

(60) Provisional application No. 61/735,088, filed on Dec. 10, 2012.

(51) Int. Cl.
*A61B 5/1455* (2006.01)
*A61B 5/103* (2006.01)
(Continued)

(52) U.S. Cl.
CPC .......... *A61B 5/1032* (2013.01); *A61B 5/1034* (2013.01); *A61B 5/1495* (2013.01);
(Continued)

(58) Field of Classification Search
None
See application file for complete search history.

(56) References Cited

U.S. PATENT DOCUMENTS

2003/0002722 A1 1/2003 Jay et al.
2007/0016079 A1 1/2007 Freeman et al.
(Continued)

FOREIGN PATENT DOCUMENTS

CN 101430274 5/2009
EP 2340763 A1 7/2011
(Continued)

OTHER PUBLICATIONS

Critchley, J., et al.; Haemoglobin colour scale for anaemia diagnosis where there is no laboratory: a systematic review; 2005; International Journal of Epidemiology; 34(6)1425-1434.
(Continued)

*Primary Examiner* — Eric Winakur
*Assistant Examiner* — Marjan Fardanesh

(57) ABSTRACT

A medical system (10) and method measures hemoglobin level of a subject (38). A hemoglobin color scale (HbCS) (22) is projected into afield of view (FOV) (42) of an imaging system (12). The HbCS (22) includes a plurality of blood color regions (26a-f), each blood color region (26a-f) corresponding to a hemoglobin level and colored to represent the color of blood at the corresponding hemoglobin level. An image of blood of the subject (38), and the projected HbCS, is acquired using the imaging system (12).

18 Claims, 3 Drawing Sheets

(51) Int. Cl.
  *A61B 5/00* (2006.01)
  *A61B 5/1495* (2006.01)
  *G01N 21/27* (2006.01)
  *G01N 21/29* (2006.01)
  *A61B 5/145* (2006.01)

(52) U.S. Cl.
  CPC ...... *A61B 5/14546* (2013.01); *A61B 5/14551* (2013.01); *A61B 5/6898* (2013.01); *A61B 5/743* (2013.01); *G01N 21/27* (2013.01); *G01N 21/293* (2013.01); *A61B 2505/01* (2013.01); *A61B 2560/0431* (2013.01)

(56) References Cited

U.S. PATENT DOCUMENTS

| | | |
|---|---|---|
| 2008/0260218 A1 | 10/2008 | Smith et al. |
| 2010/0210931 A1 | 8/2010 | Cuccia et al. |
| 2011/0218597 A1 | 9/2011 | Wang |
| 2013/0301901 A1 | 11/2013 | Satish |
| 2013/0303870 A1 | 11/2013 | Satish |

FOREIGN PATENT DOCUMENTS

| | | |
|---|---|---|
| JP | 2000-004939 | 1/2000 |
| JP | 02-280033 | 9/2002 |
| JP | 02269939 | 9/2002 |
| JP | 2011-036371 | 2/2011 |
| WO | 2008050234 A2 | 5/2008 |
| WO | 2011112559 A2 | 9/2011 |

OTHER PUBLICATIONS

University of California at Berkeley; Big Ideas at Berkeley; Assessing Hemoglobin Levels: Portable, Affordable, and Accurate Means of Assessing Hemoglobin Levels in Resource-Poor Settings; accessed Oct. 12, 2012. http://bigideas.berkeley.edu.

MEDICAL DEVICE OR SYSTEM FOR MEASURING HEMOGLOBIN LEVELS DURING ACCIDENTS USING A CAMERA-PROJECTOR SYSTEM

CROSS REFERENCE TO RELATED APPLICATIONS

This application is a national filing of PCT application Serial No. PCT/IB2013/060564, filed Dec. 2, 2013, published as WO 2014/091358 A1 on Jun. 19, 2014, which claims the benefit of U.S. provisional application Ser. No. 61/735,088 filed Dec. 10, 2012, which is incorporated herein by reference.

The present application relates generally to patient monitoring. It finds particular application in conjunction with detecting hemoglobin levels during an accident and will be described with particular reference thereto. However, it is to be understood that it also finds application in other usage scenarios and is not necessarily limited to the aforementioned application.

Hemoglobin is a key parameter used to assess blood level of a subject during an accident. However, known tests for measuring hemoglobin level are either laboratory-based or need special materials, making them unsuitable for use at an accident site. Further, known tests for measuring hemoglobin level typically require handling of blood samples. Handling blood samples poses an inherent risk of contracting a blood borne disease (e.g., Acquired Immune Deficiency Syndrome (AIDS), Hepatitis B, etc.) unless precautions are taken, which may not be possible at an accident site.

A known test for measuring hemoglobin level in low resource settings was devised by the World Health Organization (WHO). The test uses a Hemoglobin Color Scale (HbCS), shown in FIG. 1, and a particular variety of test paper for which the HbCS was designed. A drop of blood is placed on the test paper to form a stain. A clinician then compares the stain with the six colors in the HbCS by placing the stain below and/or inside the holes on the HbCS. However, this test suffers from a number of challenges.

The results of the WHO test are subjective and vary depending on environmental conditions (e.g., illumination variation). Further, the WHO test is typically not suitable for use at an accident site since the amount of blood is much higher than the single drop of blood needed for it. The large amount of blood would soak the test paper, thereby making it difficult to hold and use. Further, the HbCS and the test paper may not be readily available at an accident site.

The present application provides new and improved methods and systems which overcome the above-referenced problems and others.

In accordance with one aspect, a medical system for measuring hemoglobin level of a subject is provided. The medical system comprises at least one processor. The at least one processor is programmed to project a hemoglobin color scale (HbCS) into a field of view (FOV) of an imaging system. The HbCS includes a plurality of blood color regions, each blood color region corresponding to a hemoglobin level and colored to represent the color of blood at the corresponding hemoglobin level. The at least one processor is further programmed to acquire an image of blood of the subject, and the projected HbCS, using the imaging system.

In accordance with another aspect, a medical method for measuring hemoglobin level of a subject is provided. A hemoglobin color scale (HbCS) is projected into a field of view (FOV) of an imaging system. The HbCS includes a plurality of blood color regions, each blood color region corresponding to a hemoglobin level and colored to represent the color of blood at the corresponding hemoglobin level. An image of blood of the subject, and the projected HbCS, is acquired using the imaging system. Blood color regions of the HbCS are identified in the acquired image, and the hemoglobin level of the subject is estimated based on the identified blood color regions of the HbCS.

In accordance with another aspect, a medical system for measuring hemoglobin level of a subject is provided. The medical system includes a projection system projecting a hemoglobin color scale (HbCS) into a field of view (FOV) of an imaging system. The HbCS includes a plurality of blood color regions, each blood color region corresponding to a hemoglobin level and colored to represent the color of blood at the corresponding hemoglobin level. The medical system further includes an imaging system acquiring an image of blood of the subject and the projected HbCS. Further medical system further includes a hemoglobin module configured to identify blood color regions of the HbCS in the acquired image and estimate the hemoglobin level of the subject based on the identified blood color regions of the HbCS.

One advantage resides in measurement of hemoglobin level without the use of a laboratory.

Another advantage resides in measurement of hemoglobin level without the need for special materials.

Another advantage resides in measurement of hemoglobin level without the need to handle a blood sample.

Another advantage resides in an objective assessment of hemoglobin level.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Mobile devices are being regularly used for various healthcare applications and typically include a camera. Recently, camera-projector systems (e.g., the NIKON COOLPIX S1200PJ) have become commercially available. It is expected that camera-projection systems will become available on smart phones soon. The present application proposes to use a camera-projector system to measure hemoglobin level and overcome the above described limitations of the known tests for measuring hemoglobin level.

Figure 2:
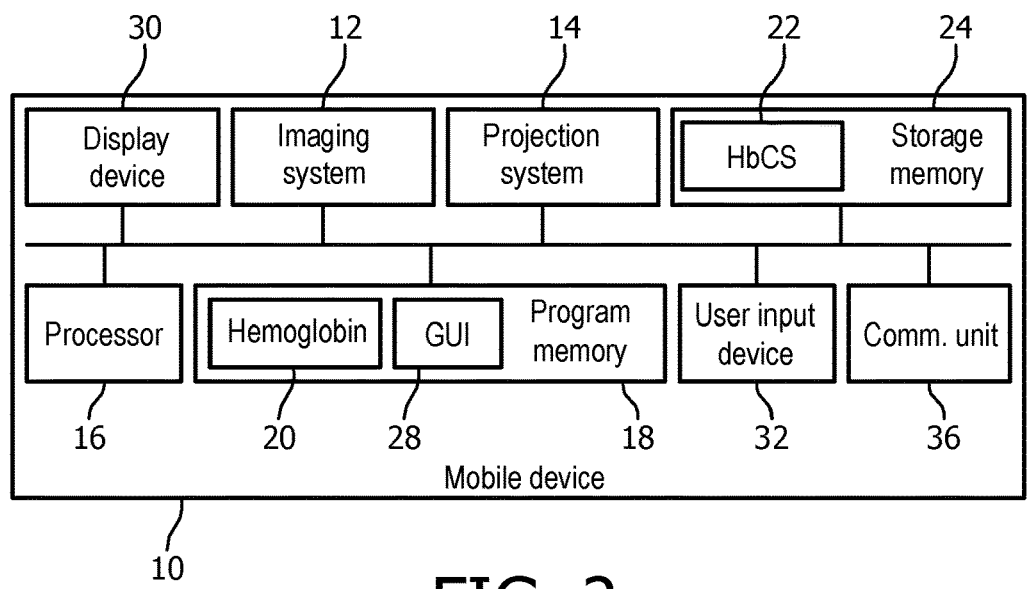
FIG. 2 illustrates a block diagram of a mobile device for measuring hemoglobin level according to aspects of the present application.

With reference to FIG. 2, a mobile device 10 includes a camera-projector system 12, 14. The mobile device 10 is, for example, a smartphone, a personal digital assistant, a digital camera, a tablet computer, a personal navigation device, etc. The camera-projector system 12, 14 includes both an imaging system 12 and a projection system 14. The imaging system 12 and the projection system 14 are configured to be operated independently.

The imaging system 12 generates image data and/or signals representing an image within a field of view (FOV). For example, the imaging system 12 can be formed from a charge-coupled device (CCD) and a lens focusing light from the FOV on the CCD. The projection system 14 projects images into the FOV in accordance with image data and/or signals from a controller 16, 18. For example, the projection system 14 can be formed from an array of a LEDs and a lens to focusing light from the array into the FOV.

The controller 16, 18 controls the camera-projector system 12, 14 to measure hemoglobin level of a subject. The controller 16, 18 includes at least one processor 16 and at least one program memory 18. The program memory 18 includes processor executable instructions executed by the processor 16. The processor executable instructions include a hemoglobin module 20, which controls the processor 16 to measure hemoglobin level of the blood sample in accordance with the method 50 of FIG. 3.

However, before beginning the method 50, the mobile device 10 is positioned so blood of the subject is within the FOV of the imaging system 12. For example, the mobile device 10 can be positioned so the FOV includes an open, bleeding wound of the subject caused by, for example, an attack or accident. As another example, where the subject is undergoing vaginal delivery, the mobile device 10 can be positioned so the FOV includes the pool of blood emanating from the vagina after the third stage of labor the aim being to estimate the amount of blood lost in postpartum hemorrhaging. Alternatively, the blood of the subject can be positioned within the FOV of the imaging system 12.

Figure 3:
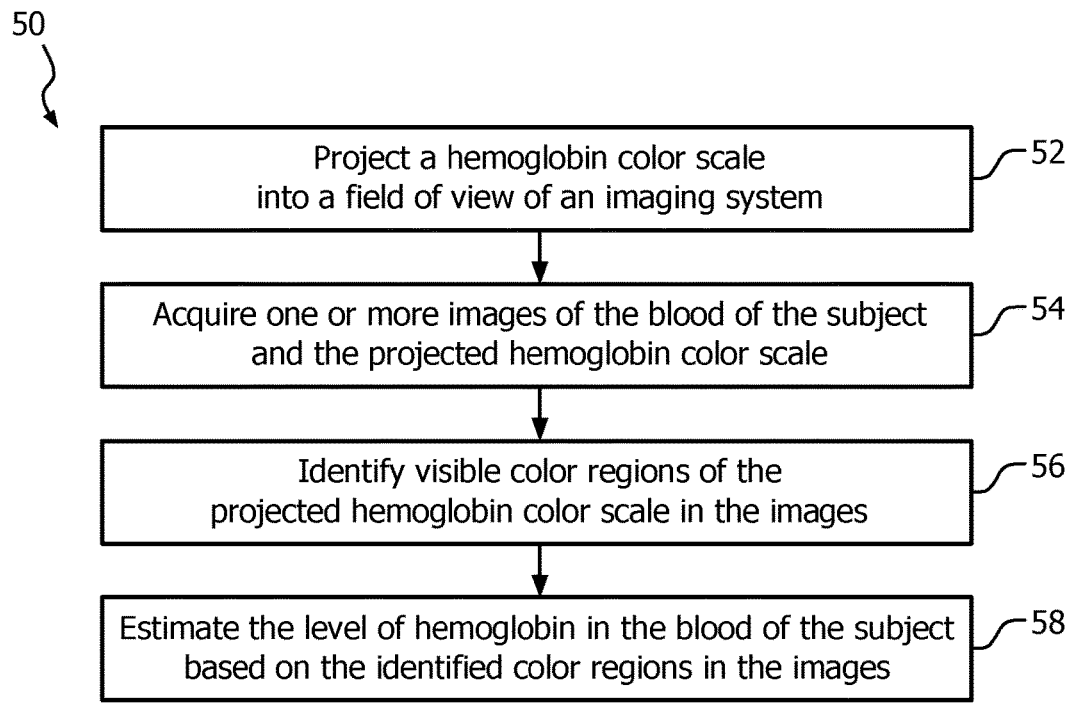
FIG. 3 illustrates a method for measuring hemoglobin level according to aspects of the present application.

With reference to FIG. 3, after positioning the mobile device 10 or the blood of the subject, the projection system 14 is controlled to project 52 a Hemoglobin Color Scale (HbCS) 22 within the FOV of the imaging system 12. Typically, the HbCS 22 is projected proximate to, adjacent to, or onto the blood of the subject. For example, the HbCS 22 could be projected onto an open, bleeding wound of the subject or, where the subject is undergoing vaginal delivery, onto the pool of blood emanating from the vagina after the third stage of labor. As another example, the HbCS 22 could be projected onto a white piece of paper proximate to blood of the subject.

Figure 4:
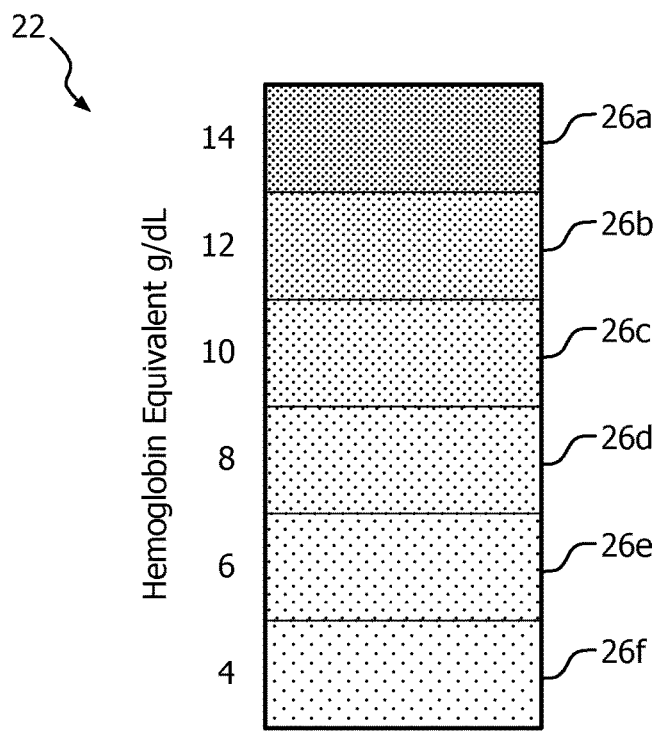
FIG. 4 illustrates an example of a projected HbCS display according to aspects of the present application.

The HbCS 22 is stored in a storage memory 24 of the mobile device 10 and includes a plurality of different blood color regions 26a-f arranged in a scale of hemoglobin level, an example of which is shown in FIG. 4. Each blood color region 26a-f corresponds to the color of blood under a different hemoglobin level (e.g., a shade of red). In some embodiments, the blood color regions 26a-f are different colors in the red-green-blue (RGB) color model (e.g., a different shade of red) or the hue-saturation-value (HSV) color model. Typically, the HbCS 22 includes six different blood color regions 26a-f corresponding to hemoglobin levels evenly spaced from 4 grams per deciliter (g/dL) to 14 g/dL, as shown in FIG. 4. The blood color regions 26a-f of the HbCS 22 are further spaced apart so there is a gap between the blood color regions 26a-f. This alleviates challenges with identifying the blood color regions 26a-f in acquired images of the HbCS 22 due to, for example, the limited computing power typical of most mobile devices.

Figure 1:
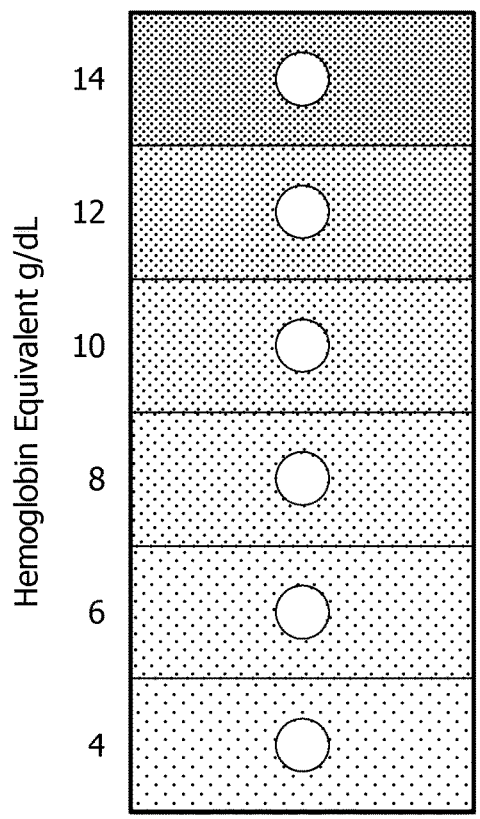
FIG. 1 illustrates an example of a paper Hemoglobin Color Scale (HbCS) card used by the World Health Organization (WHO).

While not necessary, the HbCS 22 is typically a variant of the Hemoglobin Color Scale (HbCS) used by the World Health Organization (WHO) for measuring hemoglobin. An example of the HbCS used by the WHO is shown in FIG. 1. In contrast to the HbCS used by the WHO, the HbCS 22 on the storage memory 24 does not include holes within the center of the blood color regions 26a-f. Further, the blood color regions 26a-f are spaced apart so there is a gap between the blood color regions 26a-f.

The HbCS 22 can also be augmented to include more shades of red than the six that are present in the HbCS used by the WHO since the mobile device 10 and the imaging system 12 can be more sensitive to identifying different shades of red. For example, these additional shades of red could correspond to the average value of hemoglobin between two adjacent shades of red.

Referring back to FIG. 3, after projecting the HbCS 22 into the FOV, the imaging system 12 is controlled to acquire 54 one or more images of the blood of the subject and the projected HbCS. The blood color regions 26a-f of the HbCS 22 are then identified 56 in the acquired images, typically, automatically using an intelligent image processing routine. While typically performed locally, the intelligent image processing routine can be performed by a remote computing system, the remote computing system and the medical device 10 collectively forming a medical system. Alternatively, the blood color regions 26a-f of the HbCS 22 are manually identified in the images.

When the HbCS 22 is projected directly onto the blood of the subject, one or two adjacent blood color regions 26a-f of the HbCS 22 are likely to match the color of the blood of the subject. Hence, only the remaining blood color regions 26a-f will be visible in the images and segmented. This should be considered when identifying the blood color regions 26a-f of the HbCS 22 in the images.

One approach for automatically identifying the blood color regions 26a-f of the HbCS 22 is to identify all color regions within the images. A color region of the images can be a continuous region of the images having a single color (e.g., in the RGB or HSV color model) or shade of a color. It is also contemplated that a color region can be a continuous region of similar colors (e.g., in the RGB or HSV color model). In such a situation, the single-color color regions are first identified and then the single-color color regions are clustered based on color. The single-color color regions of a cluster are replaced by the cluster color region. Typically, the blood color regions 26a-f are identified after converting the images from the RGB color model to the HSV color model. Hence, the blood color regions 26a-f are typically identified using the HSV color model.

The clustering can, for example, be performed by modeling each of the single-color color regions of the images as red, green, and blue coordinates according to the RGB color model. The points can then be clustered using any well-known clustering routine. Further, the clustering needs to distinguish between colors belonging to the different colors of the HbCS 22. In other words, the clustering must not cluster single-color color regions corresponding to the colors of the HbCS 22.

After identifying, and optionally clustering, the color regions of the images, the blood color regions 26a-f of the HbCS 22 are best matched to the color regions of the images. Matching can be performed by exhaustively generating all candidate HbCSs in the images. A candidate HbCS comprises a unique combination of a plurality of detected color regions in the images. Typically, the number of detected color regions of a candidate HbCS does not exceed the number of blood color regions of the HbCS 22. Further, the number of color regions of a candidate HbCS can vary within a predetermined range to account for blood color regions 26a-f of the HbCS 22 that are not visible in the images.

The candidate HbCSs are compared to the HbCS 22 and scored for similarity using one or more using one or more features of the HbCS 22 and candidate HbCSs. These features can include one or more of: 1) the arrangement of color regions of an HbCS relative to one another (i.e., the layout); 2) the shapes of the color regions; and 3) the colors of the color regions. For example, the layout of the HbCS 22 can be compared to the layouts of the candidate HbCSs, and higher similarity scores can be assigned to those candidate HbCSs that have similar layouts.

Similarity scores can also be weighted in favor over those candidate HbCSs that match more of the blood color regions 26a-f of the HbCS 22 matched. For example, suppose two candidate HbCSs. If one of the candidate HbCSs matches five blood color regions 26a-f of the HbCS 22 and the other only matches three blood color regions 26a-f of the HbCS 22, but the similarity scores would otherwise be the same, the similarity score of the candidate HbCS matching five blood color regions 26a-f of the HbCS 22 is greater.

When using the colors of the blood color regions 26a-f of the HbCS 22 for matching, calibration parameters can be employed to adjust the colors of the blood color regions 26a-f of the HbCS 22 to better match colors of the images, or vice versa. This can be useful because the color reproduced by the imaging system 12 and/or projection system 14 may not be the same color input into projection system 14. Calibration can be performed by projecting the HbCS 22 into the FOV, acquiring an image of the projected HbCS, manually identifying the blood color regions 26a-f in the acquired image, and determining the calibration parameters based on deviations between the color of the blood color regions 26a-f of the HbCS 22 and the color the identified color regions in the image.

After assessing all the candidate HbCS, the most similar candidate HbCS (as identified from the similarity scores) is used to estimate 58 the level of hemoglobin. This includes attempting to identify one or more blood color regions 26a-f of the HbCS that are invisible in the images. If there are such blood color regions 26a-f, an estimate of the level of hemoglobin is made based on the known hemoglobin levels associated with these invisible blood color regions 26a-f of the HbCS 22. For example, the estimated hemoglobin level can be the average of the hemoglobin levels of the invisible blood color regions 26a-f.

If there are not invisible blood color regions 26a-f (e.g., because the HbCS 22 was projected on a white piece of paper proximate the blood of the subject), a color region in the images corresponding to the blood of the subject is identified and compared using color to the blood color regions 26a-f of the HbCS 22 identified in the images. Based thereon, the best matching blood color region 26a-f of the HbCS 22 is identified. The blood can be identified manually or automatically. As to the latter, features indicative of blood can be extracted from the detected color regions and used to assess the likelihood that the color regions includes blood. Such features can include, for example, color, shape, etc. The most likely detected color region can be used for estimating hemoglobin level.

Referring back to FIG. 2, the processor executable instructions of the program memory further includes a graphical user interface (GUI) 28. The GUI 28 allows a user to control and/or otherwise interact with the mobile device 10. For example, the GUI 28 can allow the user to trigger execution of the hemoglobin module 20 to perform the method 50 of FIG. 3 and/or the GUI 28 can display the estimate of hemoglobin level. As another example, the GUI 28 can allow the user to identify color regions in the images (e.g., as the blood of the subject or as corresponding to the HbCS 22).

To allow the user to control and/or otherwise interact with the mobile device 10, the GUI 28 displays graphical elements, such as icons, windows, menus, and so on, to the user on a display device 30 of the medical device 10. Further, the GUI 28 receives user input manipulating and/or otherwise interacting with the graphical elements using a user input device 32 of the medical device 10.

At least one system bus 34 of medical device 10 interconnects the components of the medical device 10. These components include the imaging system 12, the projection system 14, the program memory 18, the processor 16, the storage memory 24, the user input device 32 and the display device 30. These components can further include a communication unit 36 (e.g., a wireless transmitter) allowing the medical device 10 to communicate with external systems and/or devices.

Figure 5:
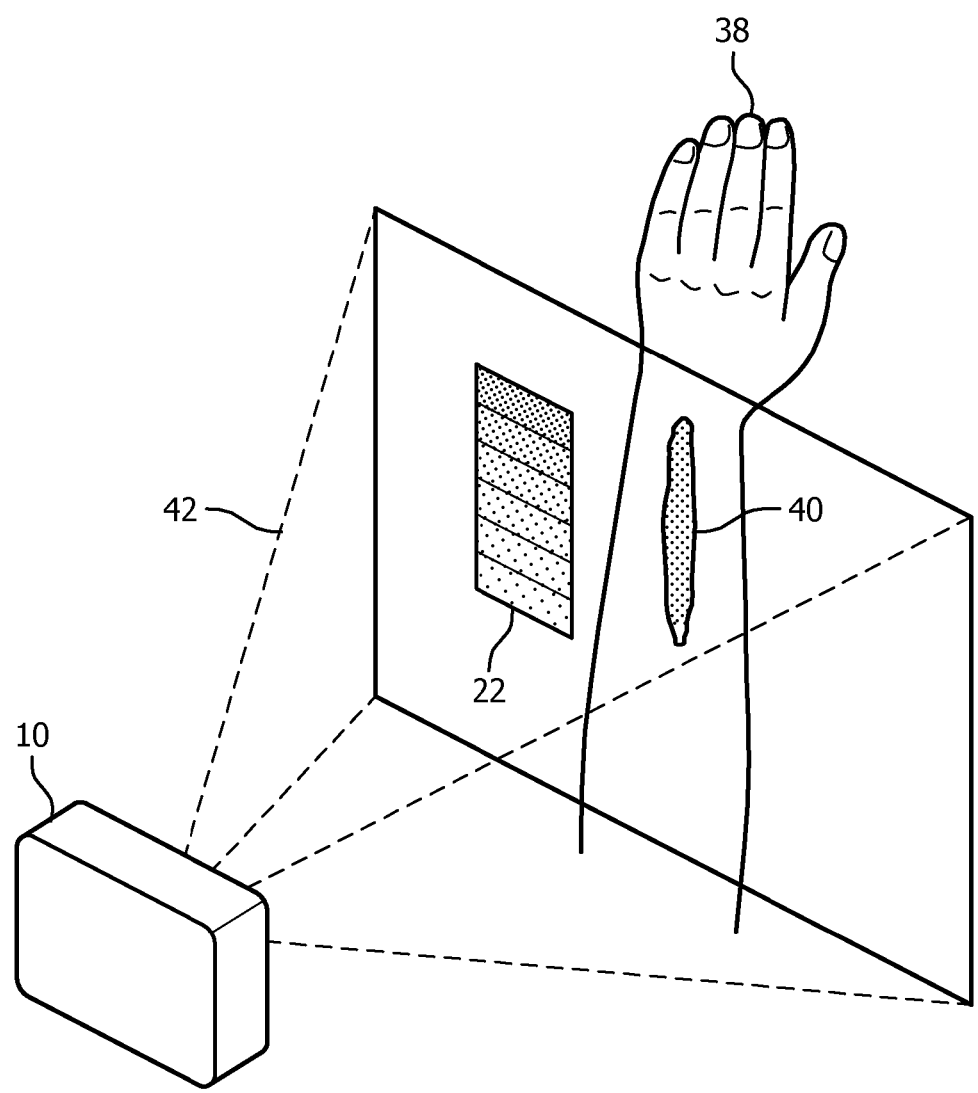
FIG. 5 illustrates a usage scenario for the mobile device of FIG. 2.

With reference to FIG. 5, an example usage scenario for the medical device 10 is illustrated. As illustrated, a portion of a subject 38 (e.g., an arm), includes a bleeding, open wound 40. Further, the medical device 10 is positioned so the wound 40 is within the FOV 42 of the medical device 10. In response to a request from a user of the medical device 10 to estimate the hemoglobin level of the subject 38, the HbCS 22 is projected adjacent to the wound 40 and one or more images are acquired. The images are then analyzed as described above to estimate the hemoglobin level of the subject 38.

In one embodiment, the analysis is performed by the processor of a smart phone controlled by software loaded as an "App". In another embodiment, a smart phone or the like sends the picture of the blood and the HbCS projection electronically to a medical professional for evaluation. The medical professional can analyze the picture visually or with a computer processor programmed, for example, as described above. In another embodiment, a person at the scene performs the analysis visually based on a companion of the projected HbCS display and the blood either directly on the victim or in the picture taken by and displayed on the display screen of the camera. The images acquired can also be transmitted to a remote computer server with higher processing power that could analyze them and report the hemoglobin level back to the mobile user.

Although the above described embodiment of the medical device 10 uses the projection system 14 to project the HbCS 20 into the FOV of the imaging system 12, in another embodiment, the projection system 14 is not used. In such an embodiment, the hemoglobin module 18 operates by attempting to find the color region 26a-f of the HbCS 22 that best matches the blood of the subject in the images. The HbCS 22 is not visibly displayed in the FOV and hence not captured in the images. Rather, the HbCS 22 is internal to the medical device 10 only. The hemoglobin level associated with the best matching color region 26a-f of the HbCS 22 is used as the estimate of the hemoglobin for the subject.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes: 1) at least one memory with processor executable instructions to perform the functionality of the controller; and 2) at least one processor executing the processor executable instructions; a display device includes one or more of a liquid crystal display (LCD), an light-emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical system for measuring hemoglobin level of a subject, said medical system comprising:
   projector configured to project a hemoglobin color scale (HbCS) onto a surface in a field of view (FOV) of an imaging system, the HbCS including a plurality of blood color regions, each blood color region corresponding to a hemoglobin level and colored to represent the color of blood at the corresponding hemoglobin level;
   an imaging system configured to acquire an image of blood of the subject together with the projected HbCS; and
   at least one processor programmed to:
      identify blood color regions of the HbCS and a region with the blood in the acquired image;
      compare a color of the imaged blood with the blood color regions; and
      estimate the hemoglobin level of the subject based on the comparison of the blood with the identified blood color regions of the HbCS.

2. The medical system according to claim 1, wherein the at least one processor is further programmed to:
   project the HbCS onto a surface of the subject with a bleeding wound or orifice of the subject, the bleeding wound or orifice within the region with the blood in the FOV.

3. The medical system according to claim 1, wherein the at least one processor is further programmed to:
   compare each of the HbCS blood color regions to the blood region of the acquired image to generate a similarity score;
   select candidate HbCS blood color regions most similar to the blood region based on the similarity scores; and
   estimate the hemoglobin level from the candidate regions.

4. The medical system according to claim 1, wherein the at least one processor is further programmed to:
   identify the blood color regions of the HbCS not visible in the acquired image based on the identified blood color regions of the HbCS; and
   estimate the hemoglobin level of the subject based on the identified blood color regions of the HbCS not visible in the acquired image.

5. The medical system according to claim 1, wherein the at least one processor is further programmed to:
   compare a color of the imaged blood to colors of each of the identified blood color regions of the HbCS to identify a most similar blood color region of the HbCS; and
   estimate the hemoglobin level of the subject from the most similar blood color region of the HbCS.

6. The medical system according to claim 1, wherein the at least one processor is further programmed to:
   generate calibrations parameters to correct color deviations between color to be projected and color in the acquired image.

7. The medical system according to claim 1, further including:
   a transmitter configured to wirelessly transmit the acquired image of the subject blood and the projected HbCS to a medical professional.

8. The medical system according to claim 1, further including at least one of:
   a display configured to display the estimated hemoglobin level; and
   a transmitter configured to transmit at least one of the estimated hemoglobin level and the acquired image to a remote location.

9. A medical method for measuring hemoglobin level of a subject, said medical method comprising:
   projecting, with a projection system a hemoglobin color scale (HbCS) into a field of view (FOV) of an imaging system, the HbCS including a plurality of blood color regions, each blood color region corresponding to a hemoglobin level and colored to represent the color of blood at the corresponding hemoglobin level;
   acquiring an image of blood of the subject, with an imaging system and the projected HbCS, using the imaging system;
   identifying blood color regions of the HbCS and a region with the blood in the acquired image;
   comparing a color of the imaged blood with the blood color regions; and
   estimating the hemoglobin level of the subject based on the comparison of the blood with identified blood color regions of the HbCS.

10. The medical method according to claim 9, further including:
    projecting the HbCS onto a bleeding wound or orifice of the subject, the bleeding wound or orifice within the FOV.

11. The medical method according to claim 9, further including with a processor:
    identifying contiguous color regions in the acquired image;
    determining candidate HbCS color regions from the identified color regions in the acquired image;
    comparing colors of each of the candidate HbCS color regions to the HbCS blood color regions to generate the similarity scores; and
    selecting the candidate HbCS color regions most similar to the HbCS blood color regions based on the similarity scores for use in estimating the hemoglobin level.

12. The medical method according to claim 11, further including:
    identifying blood color regions of the HbCS not visible in the acquired image based on the identified candidate blood color regions of the HbCS; and
    using the identified blood color regions of the HbCS not visible in the acquired image in estimating the hemoglobin level.

13. The medical method according to claim 9, further including:
    as a result of comparing the color of the identified blood color region corresponding to the blood of the subject to the color of each of the blood color regions of the HbCS identify two or more similar blood color region of the HbCS; and
    estimating the hemoglobin level of the subject from the two or more similar color regions of the HbCS.

14. The medical method according to claim 9, further including:
    generating calibrations parameters to correct color deviations between color to be projected and color in the acquired image.

15. A non-transitory computer-readable medium carrying a computer program configured to control at least one processor to perform the medical method according to claim 9.

16. The medical method according to claim 9, further including at least one of:
    displaying the estimated hemoglobin level with a display; and
    transmitting at least one of the estimated hemoglobin level and the acquired image to a remote location with a transmitter.

17. A portal electronic device comprising:
    a projector configured to project a hemoglobin color scale (HbCS) onto a surface region of a person bleeding blood, the HbCS including a plurality of projected visible colored regions, each projected region corresponding a color to one of a plurality of hemoglobin levels;
    a photographic camera configured to acquire an image including the bleeding person's blood and the projected visible colored regions;
    at least one processor configured to:
        identify in the acquired image the HbCS colored regions and the bleeding person's blood,
        compare a color of the bleeding person's blood with the HbCS color regions in the acquired image,
        estimate the hemoglobin level of blood bled by the bleeding person based on the comparison of the color of the bleeding person's blood with the HbCS colored regions in the acquired image; and
    at least one of:
        a display configured to display the estimated hemoglobin level, and
        a transmitter configured to wirelessly transmit at least one of the estimated hemoglobin level and the acquired image including the bleeding person's blood and the projected HbCS colored regions to a remote location.

18. The electronic device according to claim 17, wherein the electronic device is a smart phone.

* * * * *